United States Patent
Bishop et al.

(10) Patent No.: US 6,597,940 B2
(45) Date of Patent: Jul. 22, 2003

(54) METHODS OF DETECTING OCCLUSION OF THE CORONARY ARTERY SYSTEM AND IMAGING THE HEART

(75) Inventors: Harry Bishop, Bridgeport, WV (US); Stanislaw Majewski, Yorktown, VA (US); Marc M. Umeno, Henderson, NV (US)

(73) Assignee: NeoMed Technologies, Cleveland, OH (US)

( * ) Notice: Subject to any disclaimer, the term of this patent is extended or adjusted under 35 U.S.C. 154(b) by 0 days.

(21) Appl. No.: 09/996,602

(22) Filed: Nov. 30, 2001

(65) Prior Publication Data

US 2002/0068864 A1 Jun. 6, 2002

Related U.S. Application Data

(63) Continuation-in-part of application No. 09/726,358, filed on Dec. 1, 2000.

(51) Int. Cl.[7] .................................................. A61B 6/00
(52) U.S. Cl. ....................................... 600/436; 600/431
(58) Field of Search ................................ 600/407, 431, 600/436; 250/367, 366, 370

(56) References Cited

U.S. PATENT DOCUMENTS

| | | | | |
|---|---|---|---|---|
| 4,294,259 A | * | 10/1981 | Picunko et al. | 250/363.02 |
| 4,458,688 A | * | 7/1984 | Von Behren | 378/901 |
| H12 H | * | 1/1986 | Bennett et al. | 250/363.02 |
| 4,729,380 A | * | 3/1988 | Treves et al. | 250/432 PD |
| 5,111,818 A | * | 5/1992 | Suzuki et al. | 600/390 |
| 5,377,681 A | * | 1/1995 | Drane | 600/419 |
| 5,381,791 A | * | 1/1995 | Qian | 250/362 |
| 5,608,221 A | * | 3/1997 | Bertelsen et al. | 250/363.03 |
| 5,864,141 A | | 1/1999 | Majewski et al. | |
| 5,871,013 A | * | 2/1999 | Wainer et al. | 250/363.04 |
| 5,936,248 A | * | 8/1999 | Heukensfeldt Jansen | 250/363.03 |
| 6,180,946 B1 | * | 1/2001 | Ebstein | 250/370.11 |
| 6,271,525 B1 | | 8/2001 | Majewski et al. | |

OTHER PUBLICATIONS

Mena, I. et al., "Determination of Coronary Blood Flow Index By External Scintillation Detection", J. Nuclear Medicine, vol. 4, pp. 259–276, 1963.

Bishop, H. et al., "Evaluation of an Isotope Coronary Patency Test by Angiography", Radiology, vol. 81, No. 3, pp. 428–436, 1963.

Mena, I. et al., "Cardiac Mean Transit Times In Experimental Coronary Artery Occlusion: Deconvolution Techniques", UCLA–Harbor General Hospital, Torrance, California. Undated.

(List continued on next page.)

*Primary Examiner*—Marvin M. Lateef
*Assistant Examiner*—Barry Pass
(74) *Attorney, Agent, or Firm*—Paul V. Keller

(57) ABSTRACT

One aspect of the present invention relates to screening patients for an early stage of coronary artery disease. According to this method, a patient is screened based on the time-activity curve for a radioactive tracer passing through a left ventricle region of the patient's body. According to another aspect of the invention, an array of gamma particle detectors is employed to obtain data for a region of interest that is larger than and encompasses a left ventricle region of the patient's body. An analysis of the data identifies the subset of the region of interest that corresponds to the left ventricle region. According to a further aspect of the present invention, a second technique is employed to locate the left ventricle region. A still further aspect of the present invention relates to obtaining images of a patient's heart using a high temporal resolution gamma camera.

20 Claims, 9 Drawing Sheets

OTHER PUBLICATIONS

Pani, R., et al., "Multi–PSPMT Scintillating Camera", IEEE, Majewski, S., et al., "Initial Evaluation of a Hamamatsu Flat Panel H8500 Photomultiplier For Applications In Small High Resolution Biomedical Gamma Imagers", Draft Sep. 25, 2001.

McElroy, D., et al., "Evaluation of Performance of Dedicated, Compact Scintillation Cameras", 2000 SPIE Medical Applications of Penetrating Radiation Conference, San Diego, CA., Jul. 30–Aug. 4, 2000.

Majewski, S., et al., "Optimization of Dedicated Scintimammography Procedure Using Detector Prototypes and Compressible Phantoms", IEEE Transaction on Nuclear Science, vol. 48, Issue 3, Part 2, pp. 822–829, Jun. 2000.

Ward, J., "New Development in Portable Gamma Cameras", Advance for Radiologic Science Professionals, Aug. 3, 1998.

Pani, R., et al., "Single Photon Emission Imaging by Position Sensitive PMT", Nucl. Instr. and Meth. in Phys. Res., A. 409, pp. 524–528, 1998.

Pani, R., et al., "Multi–PSPMT Scintillation Camera", IEEE Transactions on Nuclear Science, vol. 46, No. 3, pp. 702–708, Jun. 1999.

Inoue, K., et al., "Position–Sensitive Scintillation Detector For Two–Dimensional Angular Correlation Of Annihilation Radiation Using Metal–Package Position–Sensitive Photomultiplier Tubes", Nucl., Instr. and Meth. in Phys. Res., A 423, pp. 364–368, 1999.

Nagai, S., et al., "A New Compact Position–Sensitive PMT for Scintillation Detectors", IEEE, 19999. 1997.

Raylman, R., et al., "An Apparatus for Positron Emission Mammography Guided Biopsy", IEEE, 2000.

Weisenberger, A.G., et al., "A Combined Scintimammography/Stereotactic Core Biopsy Digital X–ray System", IEEE Nuclear Science Symposium and Medical Imaging Conference, Lyon, France, Oct. 15–20, 2000.

Goode, A.R., et al., "A System for Dual Modality Breast Imaging", IEEE, 2000.

Product Brochure for SIM–400™ Scinticor, Inc. (undated).

Collimators Specification for SIM–400™ Picker International Inc. (undated).

Specifications for SIM–400™ Picker International Inc. (1996).

Product Data for SIM–400™ Picker International Inc. (1996).

Bishop, H., et al., "Effect of Early Recirculant Flow on the Shape of the First Transit Activity–Time Curve: Model Demonstration", Radioaktive Isotope in Klink und Forschung, 1978.

Mena, I., et al., "Detection of Coronary Disease Without Stressing the Patient", UCLA–Harbor General Hospital, Torrance, CA., Undated.

Mena, I., et al., "Cardiac Transit At Rest In Coronary Patients", LAC Harbor—UCLA Medical Center, Los Angeles, CA., Journal of Nuclear Medicine, Jun. 1979.

Mena, I., et al., "Detection of Coronary Disease Without Stressing the Patient", Radioaktive Isotope In Klink Und Forschung, pp. 34–46, 1980.

Syllabus, 1985 Annual Meeting of the Pittsburgh Chapter, Society of Nuclear Medicine held cojointly with the Technologist Section, Pittsburgh Chapter, SNM and the Pennsylvania College of Nuclear Medicine, May 4–5, 1985, Seven Springs, PA.

Bishop, H., "Coronary Flow Index", Excerpta Medica No. 301, 13th International Congress of Radiology, Madrid, p. 352, Oct. 1973.

Bishop, H., "Single Crystal Gamma Camera First Pass Radionuclide Angiography (FPRNA) Determination of Regional Ventricular Contractility in Acute Myocardial Infarction (AMI)", United Hospital Center, Clarksburg, WV, Proceedings of the 37th Annual Meeting, Scientific Exhibits, vol. 31, No. 5, May 1990.

85001 000 Low Profile PMT, Specifications, Burle Industries, Inc., Lancaster, PA., Undated.

* cited by examiner

BOTTOM VIEW

SIDE VIEW

METHODS OF DETECTING OCCLUSION OF THE CORONARY ARTERY SYSTEM AND IMAGING THE HEART

This application is a continuation-in-part of U.S. patent application Ser. No. 09/726,358 filed Dec. 1, 2000. The entirety of that patent application is incorporated herein by reference.

TECHNICAL FIELD

The present invention relates to medical diagnostic and screening systems and methods. In particular, the present invention relates to non-invasive cardiac imaging and functional analysis systems and methods.

BACKGROUND OF THE INVENTION

While cardiac imaging and functional analysis is the largest single nuclear medical imaging application, there remains a tremendous unmet need for improved cardiac imaging and functional analysis systems and methods. This need is exemplified by the fact that historically, for 30%–50% of those stricken with coronary artery (occlusive) disease (CAD), the first symptom of the disease is death. This has motivated considerable effort to develop diagnostic methods and apparatus to detect CAD prior to the onset of fatal symptoms and assist in the development and implementation of preventive measures.

Two strategies are presently used to reduce morbidity and mortality from CAD. The first involves screening for modifiable cardiac risk factors, such as hypertension, elevated serum cholesterol, cigarette smoking, physical inactivity, and diet. The second involves early detection of CAD. The principal tests for detecting CAD include resting and exercise ECGs, which can reveal the presence of myocardial infarctions and inducible myocardial ischemia. Tc-99m myocardial perfusion and computed tomography (CT) calcification scoring can provide visual evidence of plaques in the coronary arteries. Thallium-201 scintigraphy, exercise echocardiography, and ambulatory ECG (Holter monitoring) are less commonly used for screening purposes. None of these strategies has produced a solution to the high incidence of death due to undetected CAD. Accordingly, there remains an unsatisfied need for improved cardiac imaging and functional analysis systems and methods for reducing morbidity and mortality from CAD.

SUMMARY OF THE INVENTION

The following presents a simplified summary of the invention in order to provide a basic understanding of some of its aspects. This summary is not an extensive overview of the invention and is intended neither to identify key or critical elements of the invention nor to delineate its scope. The primary purpose of this summary is to present some concepts of the invention in a simplified form as a prelude to the more detailed description that is presented later.

One aspect of the present invention relates to a method of screening patients for an early stage of CAD. According to this method, a patient is screened based on the time-activity curve for a radioactive tracer passing through a left ventricle region of the patient's body. The time-activity curve can be analyzed by comparing it to a time-activity curve for a region of the patient's body downstream of the left ventricle, such as the patient's ascending aorta or the patient's brain. A quick transit through the patient's left ventricle region indicates an early stage of CAD wherein the free volume of the patient's coronary artery system is reduced, but the patient does not necessarily yet suffer from inducible myocardial ischemia.

Another aspect of the present invention relates to a method for obtaining a time-activity curve for a radioactive tracer passing through a left ventricle region of the patient's body. According to this method, an array of gamma particle detectors is employed to obtain data for a region of interest which is larger than and encompasses a left ventricle region of the patient's body. An analysis of data from the detector array identifies the subset of detection data that corresponds to the left ventricle region. This method avoids difficulties associated with accurately locating the left ventricle region prior to a testing or screening procedure.

A further aspect of the present invention relates to another method for obtaining a time-activity curve for a radioactive tracer passing through a left ventricle region of the patient's body. According to this method, a second technique, such as ultrasound, MRI, x-ray, computed tomography (CT), planar nuclear medicine, positron emission spectroscopy (PET), single photon emission computed tomography (SPECT), or a second radioactive tracer, is employed to locate the left ventricle region. A time activity curve is then obtained using a gamma particle detector or detector array positioned according to the determined location of the left ventricle region. Potential errors resulting from failure to accurately locate the left ventricle region are thereby avoided.

A still further aspect of the present invention relates to a method of obtaining images of a patient's heart. According to this method, the images are obtained with a high temporal resolution gamma camera. A high temporal resolution gamma camera provides diagnostically meaningful images of the patient's heart even when the high temporal resolution comes at the expense of spatial resolution. Imaging is further improved with the use of a second gamma camera at an angle to the first gamma camera. Two gamma cameras can be used to provide three-dimensional structural information, measure heart motion in three dimensions, and be used to correct for bulk movements of the patient motion in three dimensions.

Other advantages and novel features of the invention will become apparent from the following detailed description of the invention and the accompanying drawings. The detailed description and drawings provide certain illustrative examples of the invention. These examples are indicative of but a few of the various ways in which the principles of the invention can be employed.

DETAILED DESCRIPTION OF THE INVENTION

Figure 1:
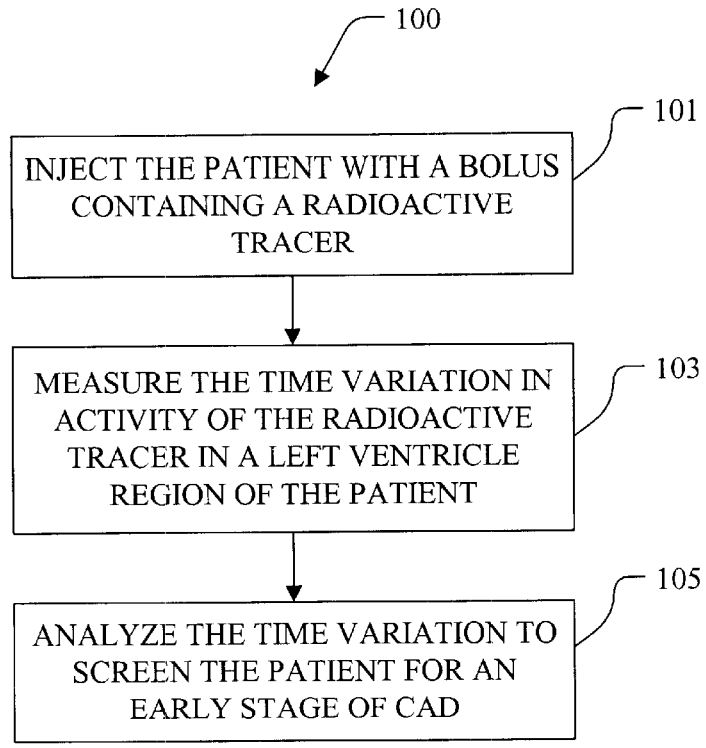
FIG. 1 is a flow chart illustrating a method of screening patients for an early stage of CAD in accordance with one aspect of the present invention.

FIG. 1 provides a flow chart illustrating a method 100 of screening patients for an early stage of CAD in accordance with one aspect of the present invention. The method involves action 101, injecting a patient with a radioactive bolus, action 103, measuring the time variation in radioactivity from the bolus in a left ventricle region of the patient's body, and action 105, analyzing the time variation to screen the patient for an early stage of CAD.

The early stage of CAD detected by method 100 is a significant occlusion of the coronary artery system that occurs before the onset of inducible myocardial ischemia. Inducible myocardial ischemia occurs when one or more major coronary arteries is restricted to a point where coronary circulation is substantially reduced. Blood flows through the coronary circulation system due to a pressure differential created by the heart. The flow passes first through the major coronary arteries, which have the largest diameters, then through minor coronary arteries, which have smaller diameters, and then through capillaries, which have the smallest diameters. In a healthy patient, the capillaries are the bottleneck of the system and primarily limit the flow rate. For inducible myocardial ischemia to occur, one or more of the largest diameter vessels, the major coronary arteries, must become almost completely occluded. The early stage of CAD detected by the present invention involves a substantial reduction in the free volume of the major coronary arteries, which may be considerably less than the degree of occlusion required to cause inducible myocardial ischemia. Of course, method 100 will also detect more advanced stages of CAD and the invention can be used to screen for more advanced stages of CAD. A significant occlusion of the coronary artery system would be one that a reasonable medical practitioner would consider as requiring close monitoring and/or treatment.

Action 101 is injecting a patient with a bolus containing a radioactive in a suitable carrier medium. The volume of the bolus is, for example, from about 1 to about 10 cc. The bolus is injected at a suitable point, for example, the antecubital vein of the right or left arm. A suitable radioactive tracer decays to produce gamma particles or alternatively positrons, which rapidly combine with electrons to produce gamma particles. Examples of suitable radioactive tracers include Tc-99m DTPA, I-131 labeled hippuran, I-123, In-111, In-113m, Tl-201, F-18 labeled fluorodeoxyglucose, Cu-62-PTSM, and O-15 labeled water. The half-lives of these tracers vary from a few minutes to a few hours. Dosages are selected with due consideration for patient health and government regulations. For example about 1 to about 20 milliCurie of Tc99m (140 keV) DTPA can be used or about 50 to about 300 microCurie of hippuran labeled with I-131 (360 keV). Higher energy tracers are preferred in that absorption correction is much less important and smaller doses can be used.

The bolus is preferably injected in such a way as to provide a single slug of tracer that circulates through the bloodstream. Although the tracer gradually disperses as it flows through the bloodstream, it is desirable to maintain as tight a dispersion as possible at the time of injection. A fractionated bolus, that is one that is separated into two or more slugs, is preferably avoided.

According to another aspect of the invention, a gamma particle detector is used to observe the shape of the injected bolus upstream of a region of interest. For example, where the region of interest is a left ventricle region, the bolus can be observed as it passes through the thorax. If the bolus shape is fractionated or otherwise unsuitable, the procedure can be aborted and/or later repeated.

Figure 2:
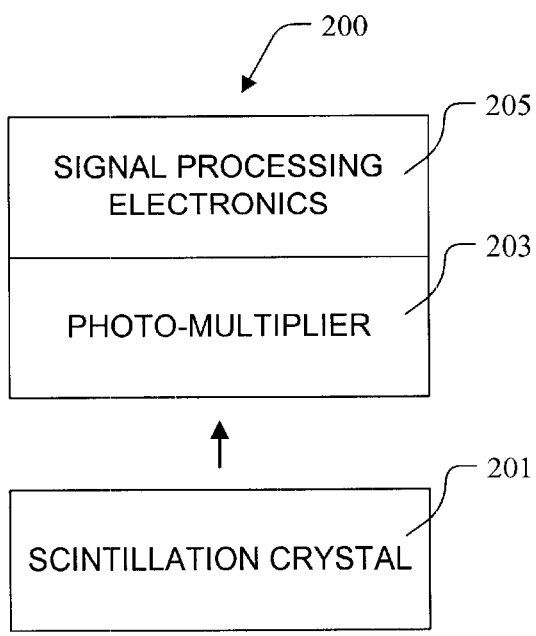
FIG. 2 a high level schematic of a gamma particle detector.

Action 103 is measuring the time variation in radioactivity from the bolus in a left ventricle region of the patient. Measuring the time variation in radioactivity involves the use of one or more gamma particle detectors. FIG. 2 provides a high level schematic of an exemplary gamma particle detector 200. Gamma particle detector 200 includes scintillation crystal 201, photo-multiplier 203, and signal processing electronics 205. Gamma particles interact with scintillation crystal 201 to produce flashes of light that are detected by photo-multiplier 203. When photo-multiplier 203 detects a flash of light, it provides a signal to electronics 205. Electronics 205 can include any combination of suitable components, such as scalers, amplifiers, and logic circuits. Scalers are typically employed to provide an output that represents number of detection events per time interval.

Figure 3:
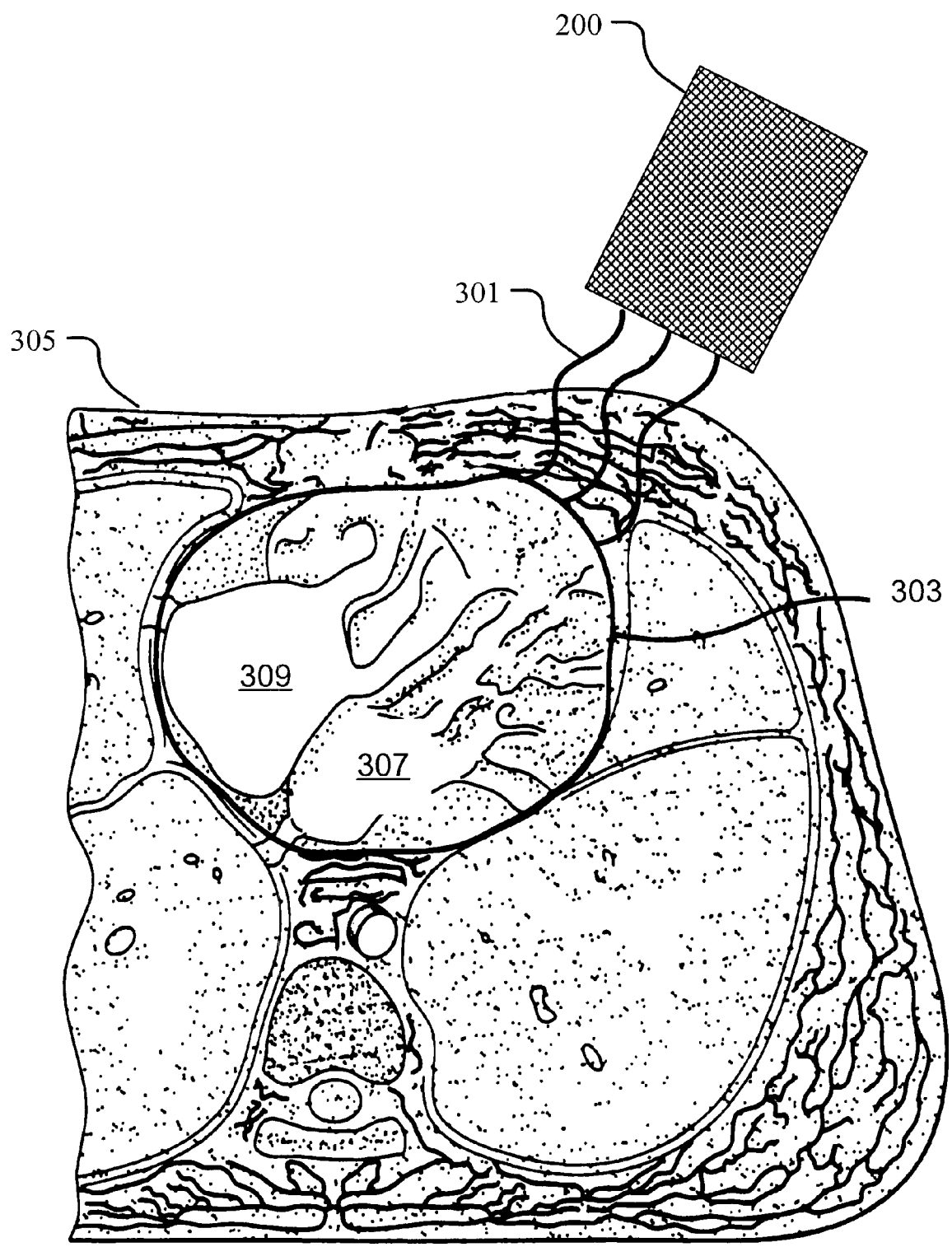
FIG. 3 illustrates, with a view from the feet, a gamma particle detector measuring the time variation in radioactivity from a left ventricle region of a patient.

FIG. 3 illustrate gamma particle detector 200 in use to measure the time variation in radioactivity from a left ventricle region of a heart 303 of patient 305. The left ventricle region substantially includes left ventricle 307 of the heart 303 while substantially excluding the right ventricle 309. Radiation 301, which is a portion of the radiation produced by the radioactive tracer, leaves the heart 303 and reaches gamma particle detector 200. Gamma particle detector 200 provides the number of gamma particles detected per unit time, which is a measure of the amount of radioactive tracer present in the left ventricle region of the heart 303. The count rate of gamma particles in excess of background levels provides the measure of radioactivity from the bolus. This measure varies over time as the bolus passes through the region of interest. Measurements are made over a period that is generally about 30 seconds or less.

The left ventricle region of the patient generally encompasses the left ventricle, although it may include only a portion of the left ventricle. As a practical matter, the left ventricle region also includes portions of the patient outside the left ventricle. The left ventricle region is selected such that the radiation detected is primarily due to radioactive tracer passing through the left ventricle and the coronary circulation system. Radioactive tracer passes through the right heart prior to passing through the left heart. Detection of radioactive tracer passing through the right heart is preferably minimized in action 103.

Scintillation crystal 201 is made with an appropriate scintillation material, for example, NaI(Tl), LSO, GSO, CsI(Tl), YSO, or CsI(Na). The scintillation material is is selected to permit detection of gamma photons with energies of at least about 60 keV. Preferably, the thickness permits detection of gamma photons with energies of about 511 keV, whereby gamma photons produced by positron-electron interactions can be detected. For example, crystals of about 2.5 cm thick NaI(Tl), about 2–3 cm thick Gadolinium Oxyorthosilicate (GSO), or about 2 cm thick Luthetium Oxyorthosilicate (LSO) can be used. GSO and LSO scintillators are faster and have higher stopping power for 511 keV photons than NaI(Tl) but are also more expensive and have lower energy resolution for lower energy photons, such as 140 keV from Tc99m.

Figure 4:
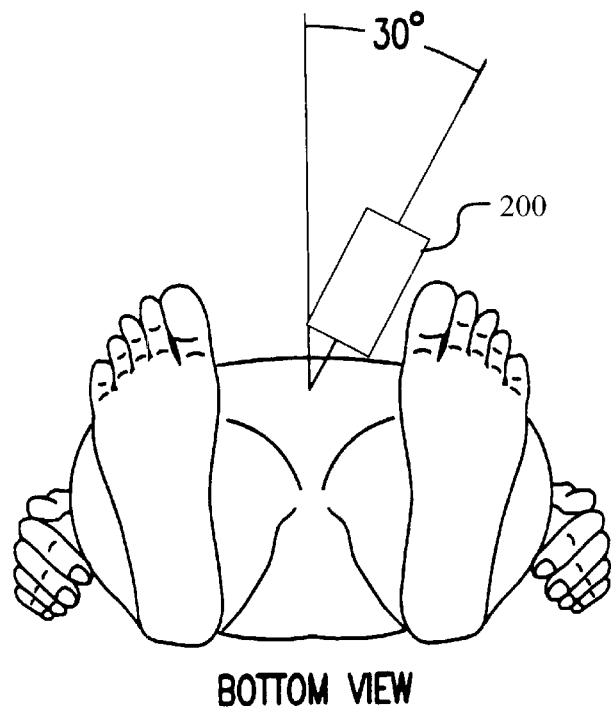
FIG. 4 is a bottom view of a patient illustrating a preferred position for a gamma particle detector in a method of screening patients for an early stage of CAD.
Figure 5:
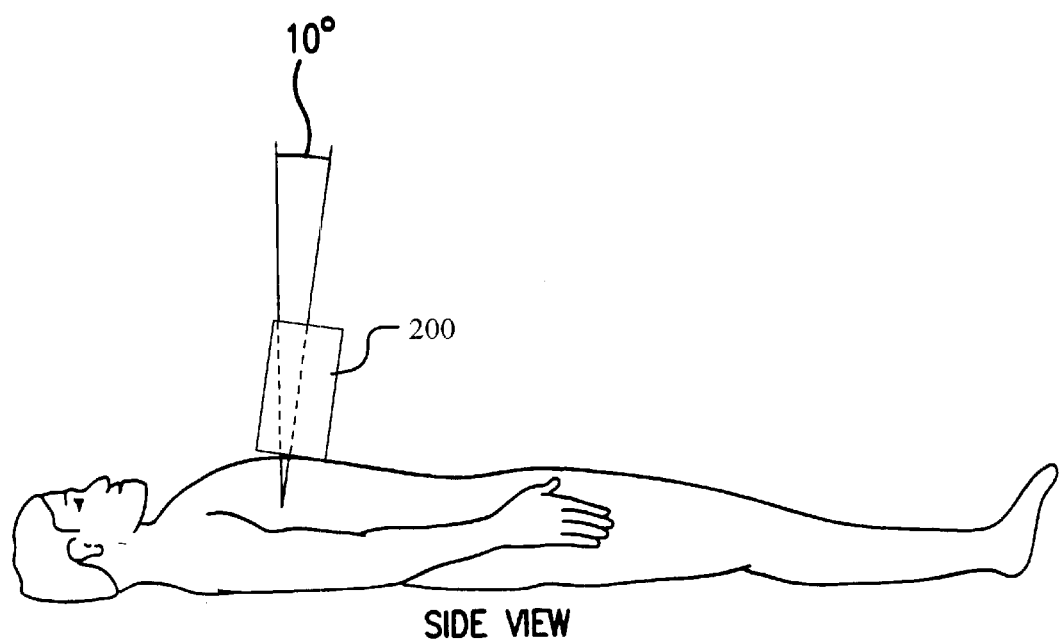
FIG. 5 is a side view of a patient illustrating a preferred position for a gamma particle detector in a method of screening patients for an early stage of CAD.

In some cases, a gamma particle detector can be directed toward the patient's left ventricle using for orientation and guidance external anatomical features, such as the locations of ribs. A preferred position of the detector 200 is approximately 30 degree right anterior oblique and in close proximity to the patient, as illustrated in FIGS. 4 and 5. This generally gives a view perpendicular to the long axis of the cardiac chamber. However, due to anatomical variations that occur among individuals, this is not always the case. Observations of external anatomical features alone do not permit consistent accurate location of the left ventricle.

According to one aspect of the invention, an array of detectors is employed, whereby data can be obtained for an array of locations that is greater than the left ventricle region or other region of interest. The array of locations can be chosen so that there is a high degree of certainty that the left ventricle region is within the array. In this context, an array of detectors includes a plurality of detectors physically arranged to collect data over a contiguous area greater than that observed by any one detector in the array. The data from the detector array can be analyzed to determine a subset of detectors in the array that substantially correspond to the left ventricle region.

Figure 6:
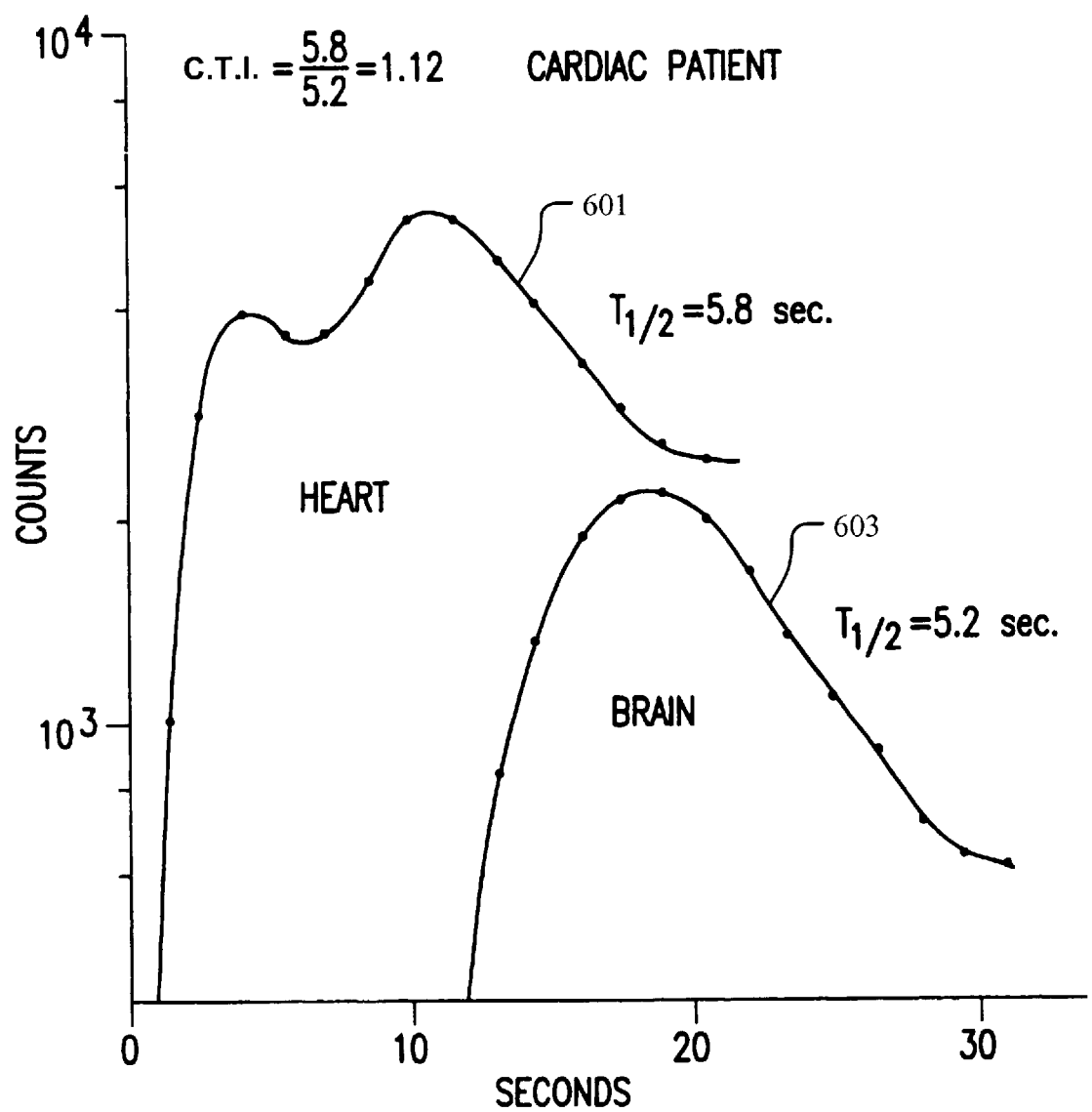
FIG. 6 is a graph show time-activity curves for the heart and brain regions of a cardiac patient.

Detector data corresponding to the left ventricle can be identified from characteristics of the time-activity curve. FIG. 6 illustrates the shape of a time-activity curve 601, which corresponds to a portion of the heart, and time-activity curve 603, which corresponds to the brain. The heart curve 601 has a characteristic double peak structure. The left peak results from flow through the right heart, while the right peak results from flow through the left ventricle.

There are a variety of methods by which time-activity curves corresponding to the left ventricle can be identified. According to one method, the left ventricle time-activity curves are those having a double peak structure and in which the height of the left peak is less than or equal to a certain fraction, about 80% for example, of the height of the right peak. More generally, left ventricle time activity curves can be identified by their functional form. Another method screens the curves according to a learning probabilistic model, such a neural net. Such a model is trained by having an expert manually review a plurality of time activity curves and identifying which do and which do not correspond to the left ventricle.

While the left ventricle region can be taken as that which corresponds to the detector that provides the data most definitively produced from the left ventricle, it is preferred that the left ventricle regions include all the detectors corresponding to the left ventricle. Using all the data increases the signal to noise ratio.

Some clustering or grouping of the detector data often takes place prior to screening for the data corresponding to the left ventricle. For example, if the detector array provides data in a 16×16 square array with 256 elements, the data may be grouped to form a 4×4 array with only 16 elements. The grouped elements have greater signal to noise ratio but lower spatial resolution. The optimal grouping can depend on the particular data set, including the location of the left ventricle within the array. Thus it can be desirable to use an iterative algorithm wherein the grouping of the array elements is redefined after a preliminary determination of the left ventricle region.

Figure 7:
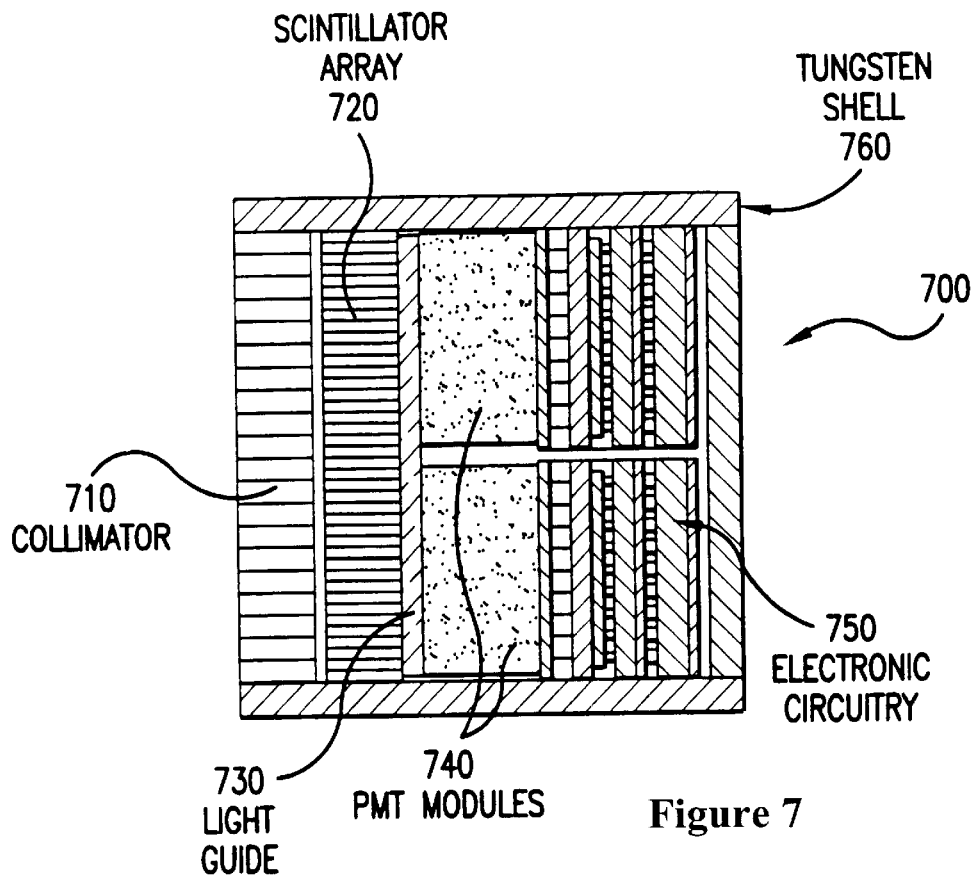
FIG. 7 is an illustration of a gamma particle detector array.

FIG. 7 is a schematic illustration of an exemplary detector array 700. Detector array 700 is also a gamma camera. Detector array 700 includes collimator 710, scintillator array 720, light guides 730, photo-multipliers 740, electronic circuitry 750, and tungsten shell 760. Gamma particles passing through collimator 710 strike scintillator array 720. Scintillator array 720 responds to the gamma particles by producing scintillation light. Light guides 730 guide the scintillation light to photo-multipliers 740. Photo-multipliers 740 produce signals in response to the light that are processed by electronic circuitry 750. Detector array 700 provides count rates for a plurality of spatially segregated positions, the spatial resolution generally being limited by collimator 710.

Scintillator array 720 generally comprises a pixellated scintillation crystal. Alternatively, a scintillator array can be constructed using an array of individual scintillation crystals. The number of elements in the array is selected according to the desired spatial resolution of the detector array 700.

Light guides 730 are employed to guide light from scintillator array 720 to photo-multipliers 740. Light guides 730 can serve to capture light that would otherwise strike between elements of a photo-multiplier array. Generally, light guides 730 are optional.

Photo-multipliers 740 produce signals corresponding to light from the scintillator array 720. The point of origin for the light within scintillator array 720 can be determined using a center of gravity calculation applied to individual signals from photo-multipliers 740. Photo-multipliers can be provided in one-to-one correspondence with scintillation array elements, in which case light guides 730 can be used to guide light from scintillator array elements to corresponding photo-multipliers.

Figure 8:
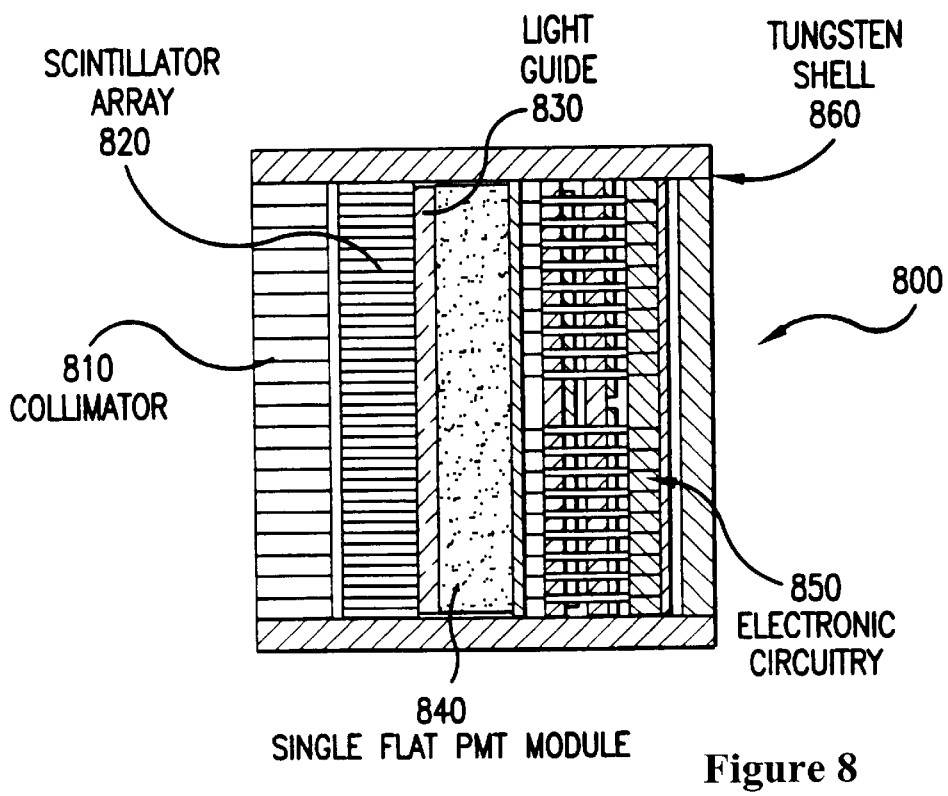
FIG. 8 is an illustration of a gamma particle detector array with a flat position sensitive photo-multiplier tube.

While a detector can employ a plurality of conventional photo-multipliers, the detector can be made substantially more compact by employing position-sensitive photo-multipliers, particularly flat position sensitive photo-multipliers. FIG. 8 illustrates an exemplary detector array 800 employing a flat position-sensitive photo-multiplier 840. In addition to flat position-sensitive photo-multiplier 840, detector array 800 includes collimator 810, scintillator array 820, light guide 830, electronic circuitry 850, and tungsten shell 860.

A position-sensitive photo-multiplier is a photo-multiplier that provides information relating to the location within the photo-multiplier's field of view where light was detected. For example, Hamamatsu Model Nos. R7600-C8, R7600-C12, R7600-M4, and R8520-C12 are suitable for use in the present invention. An array of position-sensitive photo-multipliers can also be employed. For example, a 2×2, 4×4, 6×6, 8×6, or 8×8 square array. Whenever an array of photo-multipliers is used, it is preferable that the photo-multipliers have a square, hexagonal, or other shape that allows close packing, whereby the array is compact.

Figure 9:
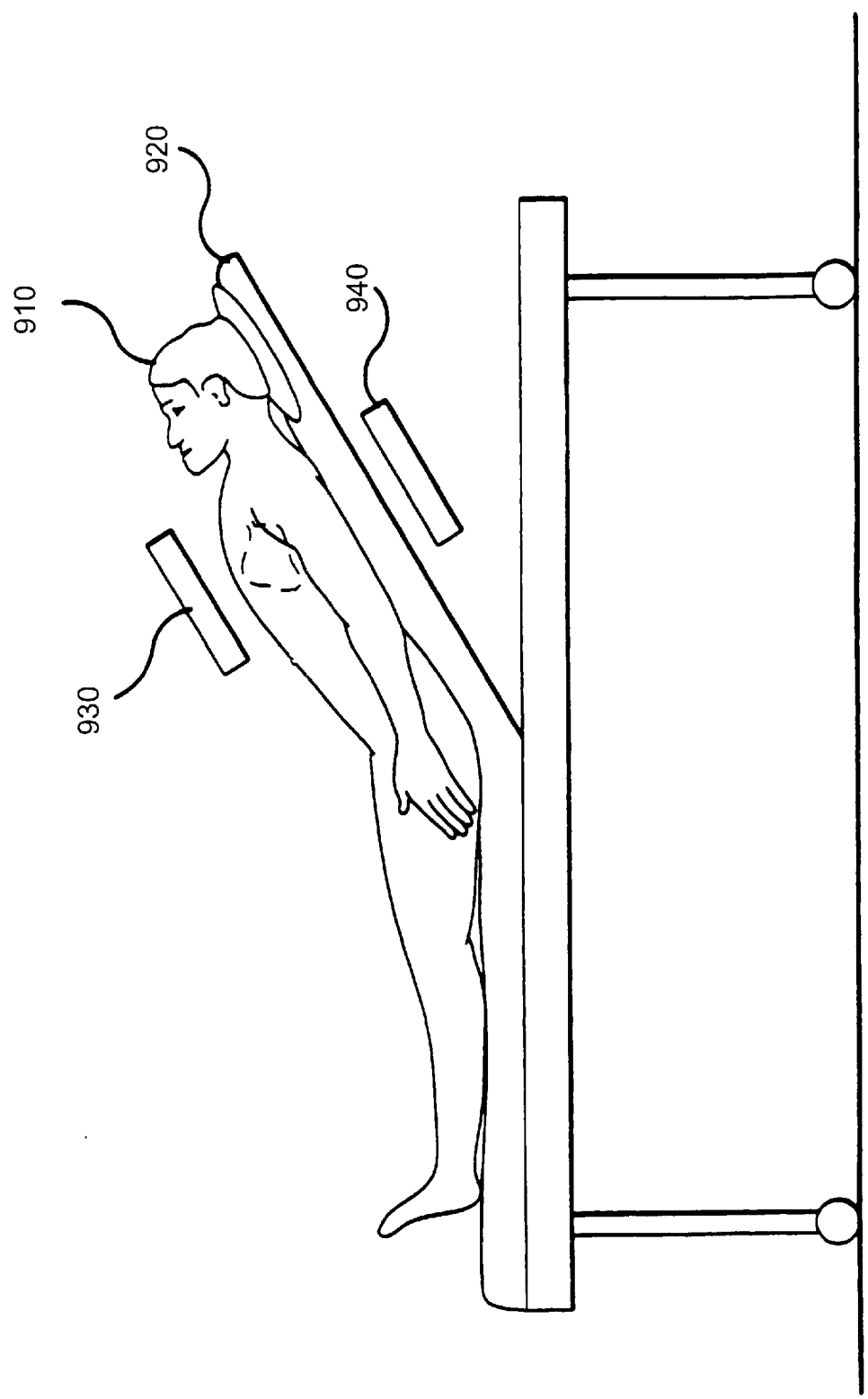
FIG. 9 illustrates the use of two gamma particle detector arrays to detect and locate positron emitters.

Detector arrays 700 and 800 do not necessarily have high spatial resolution. Spatial resolution can be sacrificed in favor of high signal to noise ratio and/or high temporal resolution. In one embodiment, a detector array provides a spatial resolution of about 1 cm or larger.

Where the radioactive tracer produces positrons, spatial resolution can be achieved without the use of collimators. When positrons combine with electrons, two gamma particles are emitted in opposite directions. By detecting both gamma particles using two gamma particle detector arrays located opposite one another, and by comparing the locations within the arrays where the gamma particles are detected, points of origin for the gamma particles can be determined. FIG. 9 illustrates a patient 910, lying on a table 920, with gamma particle detector arrays 930 and 940 facing each other and both oriented towards a left ventricle region of the patient 910, whereby positrons in the left ventricle region can be detected. Alternatively, a single detector array can be used to detect positrons, although a high-energy collimator, such as one made of tungsten, is required in order to obtain spatial resolution.

According to another aspect of the invention, a gamma particle detector is positioned for use in method 100 according to the location of a left ventricle region as determined by a suitable detection method. In this aspect of the invention, a single detector is often used instead of a detector array. The location of the left ventricle can be determined by any suitable technique, including for example ultrasound, MRI, x-ray, computed tomography, planar nuclear medicine, positron emission spectroscopy, single photon emission computed tomography, or a second radioactive tracer. For example, a small amount of Tl-201 (on the order of 50 microCurie) can be injected and the left ventricle region located based on a detector position that provides the maximum count rate. The injection used to locate the left ventricle region is generally performed 5–10 minutes before the main bolus injection.

Regardless of how the left ventricle region is located, or whether a detector array is used, method 100 is preferably carried out with one or more high temporal resolution gamma particle detectors. In one embodiment of the invention, the gamma particle detector has a temporal resolution of about 0.1 seconds or better. In another embodiment, the gamma particle detector has a temporal resolution of about 0.03 seconds or better. In a further embodiment, the gamma particle detector has a temporal resolution of about 0.01 seconds or better.

Preferably, the gamma particle detectors realize a high signal to noise ratio. The magnitude of the signal is limited in part by the amount of radioactive tracer contained in the bolus. In one embodiment, one or more detectors have a signal to noise ratio giving a measurement error of less than about 10%. In another embodiment, the measurement error is less than about 3%. In a further embodiment, the measurement error is less than about 1%. The detector head is preferably encased with ¼–½ inch thick tungsten shielding to reduce background noise.

Where a detector array is employed, the measurement error can be reduced at the cost of spatial resolution. At lower spatial resolution, each separately observed spatial region within the patient produces a sufficient number of detected radiation events within a measurement interval to produce a measurement with the required statistical accuracy. For example, if the required temporal resolution is 0.01 seconds and 1000 events per interval are required to achieve the desired signal to noise ratio, the detected event rate for a single detector must reach about 100 kHz.

The gamma particle detector, or detector array, used to obtain measurements from the region of interest is preferably portable and preferably dedicated to heart diagnosis. A unit dedicated to heart diagnosis generally takes measurements over an area about the size of the heart. In one embodiment, the detector or array takes measurements over an area of about 40 cm$^2$ or less. In another embodiment, the detector or array takes measurements over an area of about 20 cm$^2$ or less. In a further embodiment, the detector or array takes measurements over an area of about 10 cm$^2$ or less. The required data can generally be obtained in less than about 30 seconds, preferably less than about 15 seconds. Where data is sought while the patient is under stress, the short time required significantly reduces the burden on the patient as compared to other methods.

Action 105 is analyzing the data to screen the patient for an early stage of CAD. The data provides a time-activity curve for the concentration of tracer in the left ventricle region. This time-activity curve contains two contributions, one from tracer flowing through the left ventricle and another from tracer flowing through the coronary circulation system. The time activity curve can be represented by the equation:

$$A_T = V_{LV}C_{LV}(t) + V_C(D)C_C(t, D) \tag{1}$$

wherein $A_T$ is the measured activity, $V_{LV}$ is the volume of the left ventricle, $C_{LV}$ is the concentration of tracer in the left ventricle, which depends on time, t, $V_C$ is the volume of the coronary circulation system, which depends on the disease state, D, and $C_C$ is the concentration of tracer in the coronary circulation system, which depends on both time, t, and the disease state, D. Shortly after the tracer enters the left heart, the first term in equation (1) dominates because $V_{LV}$ is always larger than $V_C$. However, the residence time of the tracer in the left ventricle is much shorter than the residence time of the tracer in the coronary circulation system, typically being six to seven times shorter. Thus at longer times, the contribution of the second term becomes more apparent in the time activity curve. Functional analysis of the time activity curve, particularly at longer times, can be used to analyze the relative contributions of the two terms in Equation (1) and evaluate the disease state of the patient.

In a diseased patient, the second term of Equation (1) is diminished relative to the first term. The direct effect of the disease is that the volume, $V_C$, becomes smaller. The concentration $C_C$, is also thought to become smaller, particularly at longer times. The reason is that in the early stages of disease, the volumetric flow rate of blood through the coronary circulation system is not substantially affected; the volumetric flow rate is primarily controlled by the bottleneck presented by the capillaries. But if the volumetric flow rate remains constant while the volume of the system is reduced, the system flushes more quickly—the residence time is reduced. Thus the concentration in the coronary circulation system falls off more quickly in a diseased patient than in a healthy patient.

While it is possible to carry out Action 105, analyzing the data to screen the patient for an early stage of CAD, using only the data for the left ventricle region collected in Action 103, in a preferred embodiment of the present invention the data for the left ventricle region is analyzed by comparing it to the data for a control region. A control region is a portion of the patient downstream of the left ventricle, such as the ascending aorta or the brain, for example. Data for the control region is generally obtained using an additional gamma particle detector. The control region is selected to provide a time activity curve that is similar to that of the left ventricle apart from the coronary circulation system. As illustrated in FIG. 6, the down slope of the time-activity curve 601 for the heart region, when plotted on logarithmic scale, is greater than the down slope of the time-activity curve 603, corresponding to the brain or a similar control region. The ratio of the logarithmic scale down slope (monoexponential half-life) for the heart region to the down slope for the control region is referred to as the coronary transit index (CTI).

A low CTI, particularly one that approaches unity, indicates the presence of coronary artery disease. In one embodiment, only patients with a CTI of about 1.5 or greater pass the screen for early stage of CAD. In another embodiment, only patients with a CTI of about 1.4 or greater pass the screen. In a further embodiment, only patients with a CTI of about 1.3 or greater pass the screen.

Another aspect of the invention relates to a high temporal resolution gamma particle detector array, which is a gamma camera. The camera can be used for first pass imaging, positron imaging, quantitative myocardial perfusion measurements, planar hot spot imaging, and planar, gated, non-gated, and multi-gated pooled blood imaging. These images can be used for such purposes as measuring regional ventricular wall motion, measuring left and right ventricular ejection fractions, measuring blood flow in the myocardium, measuring regional contractivity, measuring synchrony, detecting infarct sites and abnormalities of conduction, and left to right shunt quantification.

Figure 10:
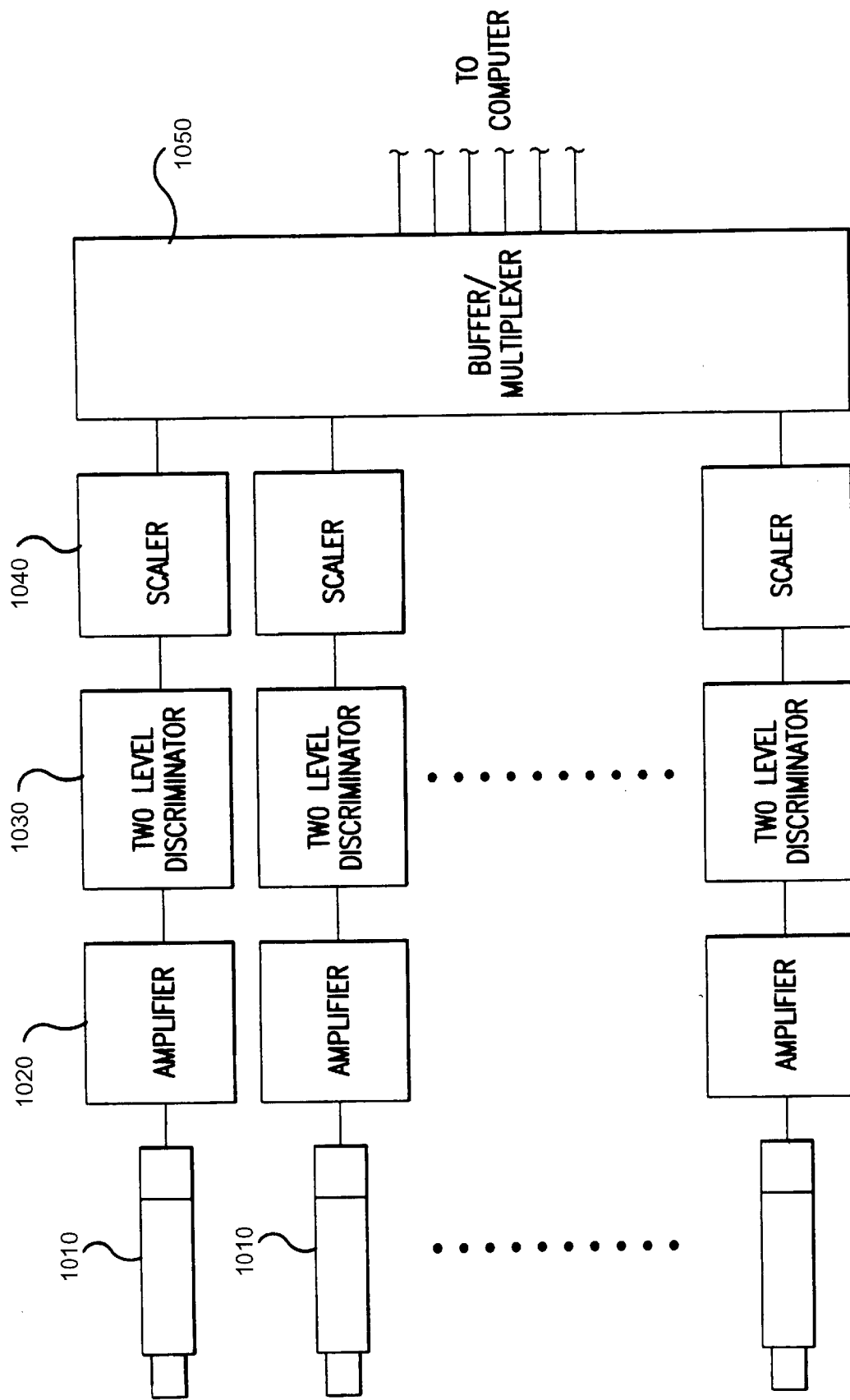
FIG. 10 is a schematic illustration of electronics for parallel processing of photo-multiplier data according to one aspect of the present invention.

High temporal resolution can be achieved, in part, by configuring the electronic circuitry for parallel processing of data from the photo-multiplier or photo-multiplier array. FIG. 10 illustrates one electronic circuitry configuration for achieving such parallel processing. In FIG. 10, each of a plurality of photo-multiplier tubes 1010 is coupled to a corresponding amplifier 1020. The amplified signals are provided to corresponding two level discriminators 1030, which distinguish those signals that have sufficient energy to correspond to the radioactive tracer in use. The output of the two level discriminators 1030 is fed to scalers 1040, which count the number of events and periodically supply output to buffer/multiplexer 1050. Buffer/multiplexer 1050 combines the count rates provided by the various scalers into a single output stream that can be provided to a computer.

Figure 11:
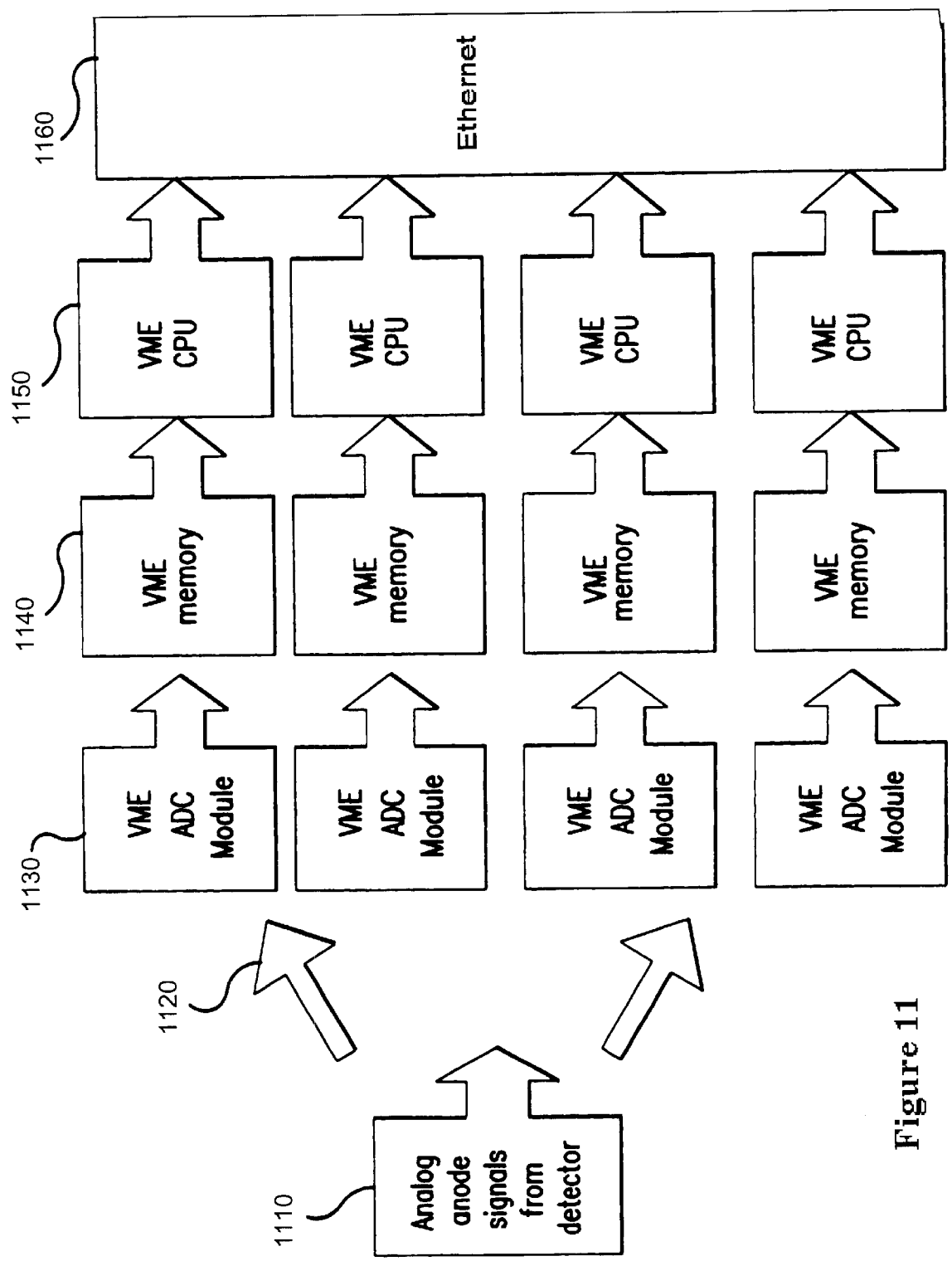
FIG. 11 is a schematic illustration of electronics for parallel processing of photo-multiplier data according to another aspect of the present invention.

Some additional options for configuring the electronic circuitry for parallel processing are illustrated in FIG. 11. FIG. 11 shows the signals coming from various anodes 1110 of one or more photo-multipliers. There does not need to be a one-to-one correspondence between parallel channels 1120 and either anodes or photo-multipliers. Rather, the signal processing can be divided in any suitable fashion. The anode signals are supplied through channels 1120 to VME analog-to-digital converter modules 1130. The digital data is accumulated in VME memories 1140 and processed by CPUs 1150. The data can then be shared across a network, such as ethernet 1160.

A gamma camera of the present invention can be made compact and portable. Such a camera can be positioned in close proximity to the heart from several different directions, which facilitates first-pass analysis and measuring ejection fractions from both left and right ventricles. A compact camera is particularly useful in intensive care units, where space is at a premium. The camera can be provided with a support gantry/harness to provide co-registration with the patient's body.

In imaging the heart, it is often desirable to compensate for patient motion. This is particularly true when heart function is being analyzed while the patient is active. One approach to compensating for patient motion is to place a radiation source on the patient's body as a point of reference. For example, an Am-241 source can be fixed to the patient's chest. The location of the source can be used to correct for patient motion in a plane perpendicular to the gamma camera. The reference source can be distinguished from the tracer, if desired, using dual energy windows.

Figure 12:
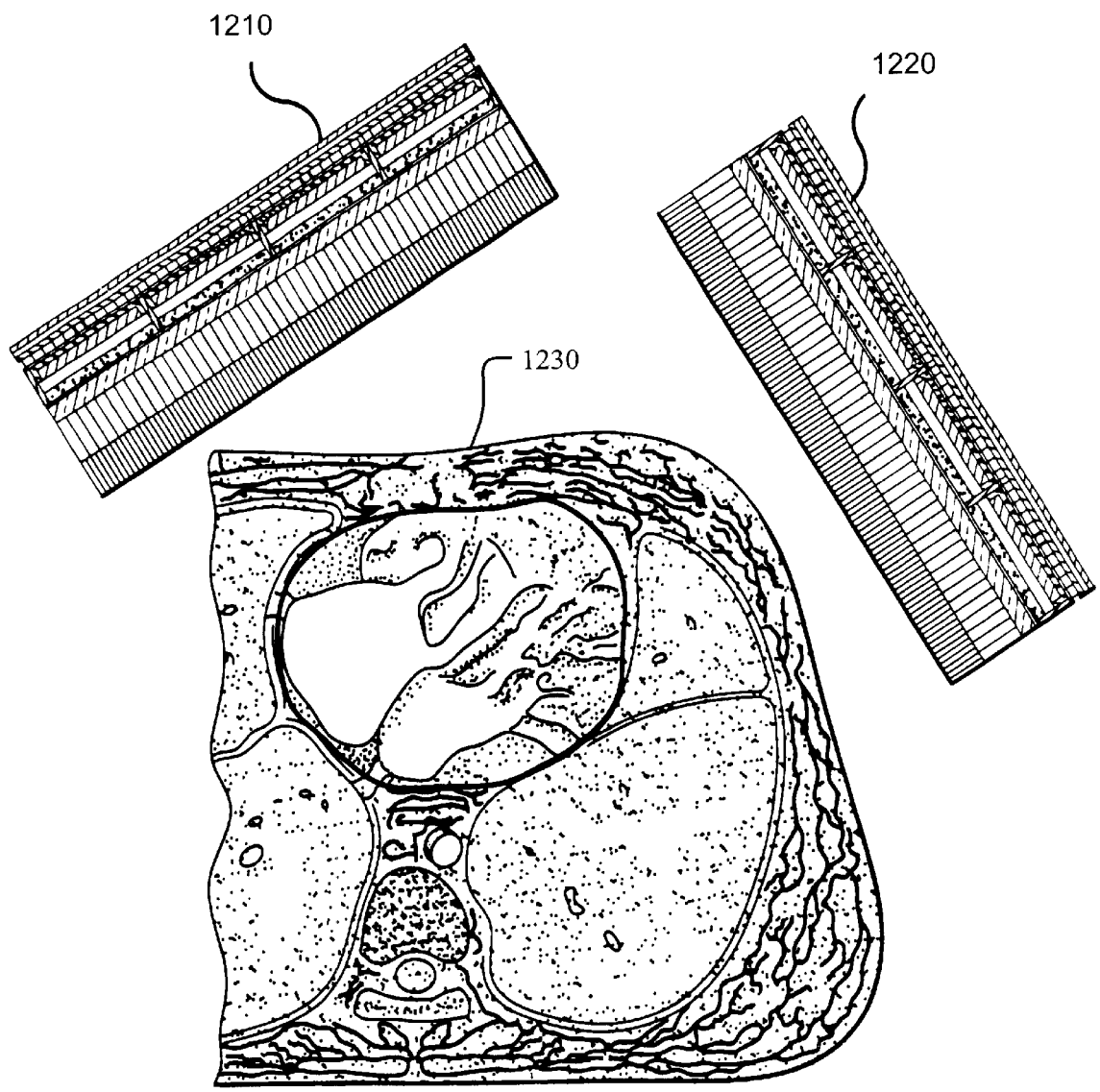
FIG. 12 is an illustration of a system that employs two gamma particle detectors.

According to a further aspect of the invention, a second camera is placed at an approximately right angle to the first camera head, whereby the system can compensate for patient motion in any direction. FIG. 12 illustrates two gamma cameras, 1210 and 1220, arranged in such a manner and oriented toward the left ventricle region of a patient's body 1230. In addition to facilitating compensation for patient motion, a second camera also allows all edges of the ventricular blood pool to be viewed simultaneously. These include the antero-lateral, apical, posterior, septal, and posterior-lateral walls. The second view also increases the accuracy of the diastolic chamber volume calculation and provides information that can be used in correcting for heart movement in first pass test procedures.

While the present invention is illustrated with particular examples, other system and methods have been described and are within the scope of the hereto appended claims. The invention and the claims are to be construed as including modifications, alterations, and equivalents that will occur to those of ordinary skill in the art upon reading and understanding this specification.

What is claimed is:

1. A method of detecting partial occlusion of a coronary circulation system in a patient having a bloodstream, comprising:
   injecting the bloodstream with a bolus comprising a radioactive tracer;
   obtaining measurements related to a time variation in concentration of the radioactive tracer for a plurality of adjacent regions in the patient that encompass an area greater than a left ventricle region;
   determining a subset of the plurality of regions that correspond to the left ventricle region; and
   assessing whether the coronary circulation system is partially occluded based at least in part on those of the measurements that correspond to the left ventricle region.

2. The method of claim 1, wherein the measurements are obtained with one or more gamma particle detectors comprising a scintillator array and one or more photo-multipliers.

3. The method of claim 2, wherein the measurements are obtained with one or more position-sensitive photo-multipliers.

4. The method of claim 2, wherein the measurements are obtained with electronics that process output from the one or more photo-multipliers in parallel.

5. The method of claim 1, wherein the measurements further correspond to a first pass of the bolus through the left ventricle region.

6. The method of claim 5, wherein the assessment is based on a time variation in concentration of the tracer in the left ventricle region as a whole.

7. The method of claim 1, wherein the assessment is based on a time variation in concentration of the tracer in the left ventricle region as a whole.

8. The method of claim 1, wherein the tracer does not absorb on vessel walls.

9. The method of claim 1, wherein the assessment is made without stressing the patient.

10. A method of detecting an early stage of occlusive coronary artery disease in a patient having a bloodstream and a heart having a left ventricle, comprising:
    determining the location of the heart by at least one of ultrasound, MRI, x-ray, computed tomography, planar nuclear medicine, positron emission spectroscopy, single photon emission computed tomography;
    using the determined location of the heart to position a gamma camera to detect gamma particles emitted from an area greater than a left ventricle region of the patient;

injecting the bloodstream with a bolus comprising a first radioactive tracer;

using the gamma camera to obtain measurements related to a time variation in concentration of the first radioactive tracer for a plurality of adjacent regions in the patient that encompass an area greater than the left ventricle region;

determining a subset of the plurality of regions that correspond to the left ventricle region; and assessing whether the coronary circulation system is partially occluded based on at least in part on those of the measurements that correspond to the left ventricle region.

11. The method of claim 10, wherein the position of the heart is determined by ultrasound.

12. The method of claim 10, wherein the position of the heart is determined by a process involving the detection of a second radioactive tracer, which is different from the first radioactive tracer.

13. A method of screening a patient for an early stage of coronary artery disease, comprising:

injecting the patient with a bolus comprising a radioactive tracer;

measuring a first time variation in a concentration of the radioactive tracer in a left ventricle region of the patient;

measuring a second time variation in the concentration of the radioactive tracer in a second region of the patient located downstream of the left ventricle region; and comparing the first time variation and the second time variation to screen the patient for coronary artery disease, including some stages of the disease occurring before the onset of inducible myocardial ischemia.

14. The method of claim 13, further comprising:

measuring a second time variation in a concentration of the radioactive tracer in a second portion of the patient located downstream of the left ventricle region; and computing a CTI from the first time variation and the second time variation and using the CTI to screen the patient for the early stage of coronary artery disease.

15. The method of claim 13, wherein the first time variation corresponds to a first pass of the bolus through the left ventricle region.

16. The method of claim 15, wherein the left ventricle region includes the entire left ventricle.

17. The method of claim 13, wherein the left ventricle region includes the entire left ventricle.

18. The method of claim 13, wherein the tracer does not absorb on vessel walls.

19. The method of claim 13, wherein screening is accomplished without stressing the patient.

20. A method of detecting coronary artery disease, comprising:

injecting the bloodstream with a bolus comprising a radioactive tracer;

employing a first gamma particle detector to determine the bolus shape as it passes a point upstream of a heart;

determining whether the bolus shape is satisfactory for a bolus transit time measurement; and if the bolus shape is satisfactory, measuring the bolus transit time with a second gamma particle detector and detecting coronary artery disease from the bolus transit time.

* * * * *